United States Patent [19]

Merle

[11] Patent Number: 5,482,914
[45] Date of Patent: Jan. 9, 1996

[54] HYDROPHOBIC ADSORBENTS AND THEIR USE FOR THE ADSORPTION OF LIPOPROTEINS

[75] Inventor: Peter Merle, Marburg, Germany

[73] Assignee: Behringwerke Aktiengesellschaft, Marburg, Germany

[21] Appl. No.: 177,947

[22] Filed: Jan. 6, 1994

[30] Foreign Application Priority Data

Jan. 9, 1993 [DE] Germany ............... 43 00 412.1

[51] Int. Cl.$^6$ ................................ B01J 20/22
[52] U.S. Cl. .............. 502/404; 502/402; 210/502.1; 210/679; 530/359; 536/55.1
[58] Field of Search ................ 502/401, 402, 502/404; 210/502.1, 679; 530/359; 536/55.1

[56] References Cited

U.S. PATENT DOCUMENTS

| | | |
|---|---|---|
| 4,09,583 | 6/1977 | Chang et al. . |
| 4,654,420 | 3/1987 | Furuyoshi et al. ............ 210/692 |
| 4,696,958 | 9/1987 | Gurske . |
| 4,814,077 | 3/1989 | Furuyoshi et al. ............ 502/401 |
| 5,030,352 | 7/1991 | Varady et al. . |

FOREIGN PATENT DOCUMENTS

| | | |
|---|---|---|
| 0137221A2 | 4/1985 | European Pat. Off. . |
| 0263184 | 4/1988 | European Pat. Off. . |
| 0424698A1 | 5/1991 | European Pat. Off. . |
| 1066459 | 4/1967 | United Kingdom . |

WO91/19565  12/1991  WIPO .

OTHER PUBLICATIONS

"Properties of Detergents", Helenius et al., Methods in Enzymology, LVI, 734–749.

"Hydrophobic Interaction Chromatography—The Synthesis and the Use of Some Alkyl and Aryl Derivatives of Agarose", Hjertén et al., *Journal of Chromatography*, 101:281–288(1974).

*Primary Examiner*—Anthony McFarlane
*Attorney, Agent, or Firm*—Finnegan, Henderson, Farabow, Garrett & Dunner

[57] ABSTRACT

Adsorbents composed of a polysaccharide support which is suitable for chromatography and is preferably based on agarose which has undergone a chemical reaction with the glycidyl ethers of nonionic polyoxyethylene detergents of the type HO—$(CH_2CH_2O)_n$—O—R to give a compound of the formula I $$(polysaccharide)\text{-}OCH_2\text{-}CH(OH)\text{-}CH_2O\text{-}(CH_2\text{-}CH_2\text{-}O)_n\text{-}OR \quad (I)$$

where
  n is an integer from 2 to 30 and
  R is an alkyl radical having 4–20 or a phenyl radical or a phenylalkyl radical, where the alkyl radical has 1–16 carbon atoms, to a process for their preparation and to their use for removing lipoproteins from human or animal body fluids are described.

12 Claims, No Drawings

HYDROPHOBIC ADSORBENTS AND THEIR USE FOR THE ADSORPTION OF LIPOPROTEINS

The invention relates to adsorbents composed of a polysaccharide support which is suitable for chromatography, and is preferably based on agarose which is subjected to a chemical reaction with the glycidyl ethers of nonionic polyoxyethylene detergents of the type HO—$(CH_2CH_2O)_n$—O—R, to a process for their preparation and to their use for removing lipoproteins from human or animal body fluids.

Storage of body fluids such as, for example, serum, plasma, cerebrospinal fluid, pleural exudate or ascites of human or animal origin may result in deposits or turbidities which considerably impair the quality of these products. The lipoprotein macromolecules occurring in body fluids are regarded as partly responsible for these instabilities, and they display a tendency to aggregation per se because of their content of phospholipids which are insoluble in water.

Removal of the lipoproteins from the abovementioned fluids as a rule leads to good storage stability.

Furthermore, a number of medical diagnostic tests are susceptible to interference on use of patients' samples with a high lipoprotein content.

The presence of lipoproteins may also impede or prevent the processing of biological materials to pharmaceuticals or diagnostic test components.

There has been no lack of attempts in the past to develop methods suitable for removing lipoproteins, especially from sera or plasmas. However, these known methods have disadvantages which restrict or render impossible their industrial use:

a) Extraction with liquid halohydrocarbons (for example Lipoclean®) is objectionable for environmental-protection reasons.

b) Absorption with dextran sulfate is not quantitative for all lipoproteins.

c) Octyl- or phenyl-Sepharose® has a low capacity and can be regenerated only in an elaborate procedure.

d) The method described in EP 137221 using a polyhydroxymethylene derivative is suitable for the process in chromatography columns only with restrictions; the material can be regenerated only with difficulty.

e) Methods which operate with silicon dioxide adsorbents are unsuitable for plasma because coagulant proteins such as, for example, fibrinogen are also bound.

f) The method of flotation of lipoproteins in an ultracentrifuge requires very costly equipment and provides only a low throughput.

The aim of the present invention was to prepare an adsorbent which permits the lipoproteins to be removed quantitatively from untreated biological fluids with a high throughput. It was moreover intended that the adsorbent be easy to regenerate and display high and reproducible capacities.

It was intended that it be possible to obtain, without damage, the lipoproteins desorbed from the adsorbent in the regeneration process so that it would be possible to use them as raw materials for producing diagnostic tests or therapeutic products.

The present invention relates to adsorbents for the removal of lipoproteins from human or animal body fluids, composed of a polysaccharide support which is suitable for chromatography and is preferably based on agarose which has undergone a chemical reaction with the glycidyl ethers of nonionic polyoxyethylene detergents of the type HO—$(CH_2CH_2O)_n$—O—R.

Adsorbents of this type can be represented in particular by the formula I

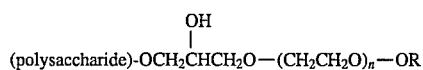

(polysaccharide)-OCH$_2$CHCH$_2$O—(CH$_2$CH$_2$O)$_n$—OR with OH where n is an integer from 2 to 30, preferably 6 to 20, and R is an alkyl radical having 4–20, preferably having 10–16, carbon atoms or a phenyl radical or a phenylalkyl radical, where the alkyl radical has 1–16 carbon atoms and is preferably tert-octyl.

The support polysaccharide is preferably a macroporous agarose gel with an agarose content of 1–6%. It is advantageous to use Sepharose® of the type CL-2B.

Examples of suitable polyoxyethylene detergents are known under the proprietary names Brij®, Genapol®, Nonidet®, Tergitol® or Triton®. These proprietary products are not homogeneous and comprise a mixture of ethers in which the polyoxyethylene chain length differs. The manufacturers indicate in each case the main component or a chain-length range. The structure and composition of polyoxyethylene detergents of these types is described in Methods in Enzymology, LVI, 734–749.

The glycidyl ethers of the detergents have the formula II

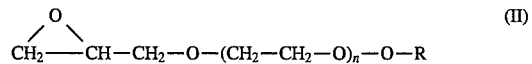

The invention also relates to a process for the preparation of the adsorbents according to the invention.

The reaction of alcohols or phenols with epichlorohydrin to give the alkyl or phenyl glycidyl ethers is described in the Journal of Chromatography, 101 (1974) 281–284. This process can be used to prepare the glycidyl ethers of the nonionic detergents described above. This entails the nonionic detergent being heated with an epihalohydrin such as epichlorohydrin in the presence of a Lewis acid such as BF$_3$ etherate, and subsequently reacted in the presence of NaOH at room temperature to give the glycidyl ether derivative. The reaction scheme is generally described below (HO—R$^1$=detergent):

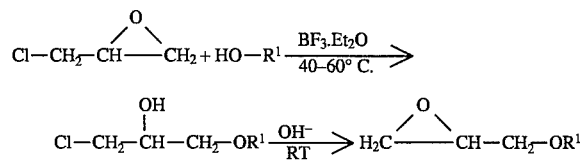

The process for alkyl or phenyl glycidyl ethers which is described in Journal of Chromatography, 101 (1974) 281–288 can be used for the reaction of the glycidyl ethers of the nonionic detergents with a polysaccharide. This entails the dehydrated polysaccharide being suspended in an anhydrous inert solvent, for example dioxane, and reacted with the glycidyl ether of a nonionic detergent in the presence of BF$_3$ etherate:

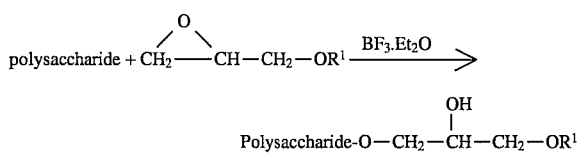

$$\text{Polysaccharide-O}-CH_2-\underset{\underset{OH}{|}}{CH}-CH_2-OR^1$$

The polysaccharide derivative (adsorbent) according to the invention is transferred into an aqueous medium and is ready for use.

It is advantageous to pack the adsorbents according to the invention in a chromatography column or in a cartridge for the adsorption of lipoproteins from biological fluids.

However, it is also possible to carry out the adsorption of the lipoproteins by direct addition of the adsorbents to biological fluids. The adsorbent can also be added in dry form for this purpose.

After the biological fluids have been contacted with an adsorbent according to the invention in one of the above-mentioned methods, they are obtained as clear lipoprotein-free fluids.

After adsorption onto an adsorbent, the lipoproteins can be eluted with solutions of substances which split hydrophobic linkages. Examples of these are solutions of ionic or nonionic detergents, of urea, KSCN or guanidine. HCl or solutions of alcohols such as ethylene glycol.

The substances preferably chosen are those which cause no denaturation of the lipoproteins. Rapid and quantitative elution is achieved on use of a solution of the nonionic detergent whose glycidyl ether was employed for the derivatization of the polysaccharide.

EXAMPLES

1. Preparation of the glycidyl ethers of Genapol® T250

10g of Genapol® T250 were dissolved in 40 ml of anhydrous dioxane, and 1 ml of $BF_3$ etherate was added. The mixture was heated to 50° C. in a round-bottom flask with drying tube attachment and magnetic stirrer. 2 ml of epichlorohydrin were added, and the mixture was stirred at 50° C. for 2 h.

The mixture was subsequently cooled to room temperature, and 4 g of NaOH pellets were added. The mixture was stirred at room temperature for 1.5 h.

After centrifugation of the mixture in a bench centrifuge it was possible to obtain the solution of the glycidyl ether of Genapol® T250 in dioxane as the supernatant.

2. Dehydration of Sepharose® CL-2B 150 ml of an aqueous suspension of Sepharose® CL-2B were packed in a glass chromatography column and subsequently washed with the following solutions under gravity:

a) 1 column volume of water b) then 1 column volume of 25% ethanol in water c) then 1 column volume of 50% ethanol in water d) then 1 column volume of 96% ethanol in water e) finally 2 column volumes of anhydrous dioxane.

The dehydrated Sepharose® CL-2B from the column was placed in a vessel and stored with exclusion of moisture until used.

3. Coupling of the glycidyl ether of Triton® X-100 to Sepharose® CL-2B 100 g of Sepharose® dehydrated as in Example 2 were suspended in 100 ml of anhydrous dioxane in a closed stirring vessel and 2 ml of $BF_3$ etherate and 10 ml of a 20% strength solution of the glycidyl ether of Triton® X-100 in dioxane were added, and the mixture was slowly stirred at room temperature for 2 h. The derivatized gel was then packed into a glass chromatography column and washed with the following solutions:

a) one column volume of dioxane one column volume of 96% ethanol in water one column volume of 50% ethanol in water one column volume of 25% ethanol in water.

The derivatized gel was stored in 25% ethanol at 4° C. until used.

4. Adsorption of the lipoproteins from human citrated plasma

A chromatography column (4×30 cm) was packed with 120 ml of a Triton® X-100 derivative of Sepharose® CL-2B and equilibrated with a buffer composed of 0.9% NaCl, 10 mM sodium citrate, pH 7.0, called buffer A hereinafter.

The column was charged with 360 ml of a fresh human citrated plasma at a flow rate of 6 ml/min. It was then washed with buffer A.

Fractions with maximum absorption were collected. It was possible to obtain 320 ml of a clear human plasma in which neither cholesterol (Monotest® cholesterol, Boehringer: <2.5 mg/dl) nor apolipoprotein A-I and apolipoprotein B (nephelometric tests, Behringwerke AG: ApoAl <5 mg/dl; ApoB <7.3 mg/dl) were detectable.

5. Delipidation of rabbit serum 400 ml of rabbit serum were passed through a column as described in Example 4, maintaining a flow rate of 5 ml/min. Fractions with maximum protein concentration were collected. The column was then washed with buffer A. It was possible to obtain 360 ml of a clear rabbit serum in which cholesterol was no longer detectable (<2.5 mg/dl).

6. Elution of the lipoproteins

A column as described in Example 4 and loaded with human lipoproteins was washed with buffer A until the eluate reached the base line absorption. The lipoproteins were then eluted from the column in a buffer composed of buffer A with 1% Triton® X-100. Fractions with maximum absorption were collected. It was possible to obtain a lipoprotein concentrate which contained about 80% of the loaded lipoproteins in a concentration which was about twice that in the loaded plasma.

I claim:

1. An absorbent for the removal of lipoproteins form human or animal body fluids, which comprises a polysaccharide support which is suitable for chromatography, wherein said polysaccharide support comprises the chemical reaction product of the polysaccharide (itself) with a glycidyl ether of a nonionic polyoxyethylene detergent.

2. An adsorbent as claimed in claim 1 having the formula I

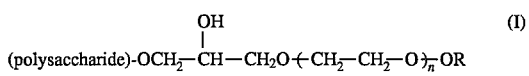

where n is an integer from 2 to 30 and

R is an alkyl radical having 4–20 carbon atoms or a phenyl radical or a phenylalkyl radical, where the phenylalkyl radical has 1–16 carbon atoms.

3. An adsorbent as claimed in claim 2, wherein n is an integer from 6 to 20.

4. An adsorbent as claimed in claim 2, wherein R is an alkyl radical having 10–16 carbon atoms.

5. An adsorbent as claimed in claim 2, wherein the polysaccharide support is a macroporous agarose gel with an agarose content of 1–6%.

6. A process for the preparation of an adsorbent of the formula I in claim 2, which comprises reacting a detergent of the formula III

 (III)

where n is an integer from 2 to 30 and

R is an alkyl radical having 4–20 carbon atoms, a phenyl radical or a phenylalkyl radical, where the phenyalkyl radical has 1–16 carbon atoms; with epichlorohydrin to give a glycidyl ether of the formula II

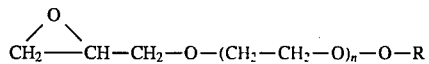 (II)

and reacting this glycidyl ether in the presence of a Lewis acid with a polysaccharide support to give a compound of the formula I.

7. An adsorbent as claimed in claim 1, wherein the glycidal ether is of the formula HO—($CH_2$—$CH_2$—$O_n$)—O—R.

8. An adsorbent as claimed in claim 2, wherein the phenylalkyl radical having 1–16 carbon atoms is tert-octyl.

9. A process according to claim 6, wherein n is an integer from 6 to 20.

10. A process according to claim 6, wherein R is an alkyl radical having 10 to 16 carbon atoms.

11. A process according to claim 6, wherein the polysaccharide support is a macroporous agarose gel with an agarose content of 1 to 6%.

12. An adsorbent according to claim 1, wherein said polysaccharide is agarose.

* * * * *